United States Patent [19]

Papenfuhs et al.

[11] Patent Number: 5,276,203
[45] Date of Patent: Jan. 4, 1994

[54] PROCESS FOR THE PREPARATION OF 1,2-BIS-(2-NITROPHENOXY)-ETHANE

[75] Inventors: Theodor Papenfuhs, Frankfurt am Main; Wilfried Pressler, Kelkheim; Jochen Rapp, Frankfurt am Main, all of Fed. Rep. of Germany

[73] Assignee: Hoechst Aktiengesellschaft, Frankfurt am Main, Fed. Rep. of Germany

[21] Appl. No.: 957,723

[22] Filed: Oct. 7, 1992

[30] Foreign Application Priority Data

Oct. 9, 1991 [DE] Fed. Rep. of Germany ....... 4133446

[51] Int. Cl.$^5$ ..................... C07C 205/06; C07C 41/01
[52] U.S. Cl. ................................................... 568/586
[58] Field of Search .............................. 568/644, 586

[56] References Cited

U.S. PATENT DOCUMENTS 4,695,656 9/1987 Reh et al. ........................... 568/587

FOREIGN PATENT DOCUMENTS 1539183 1/1979 United Kingdom .

*Primary Examiner*—Marianne M. Cintins
*Assistant Examiner*—Margaret J. Page
*Attorney, Agent, or Firm*—Connolly & Hutz

[57] ABSTRACT

The present invention relates to a process for the preparation of 1,2-bis-(2-nitrophenoxy)-ethane, by reacting 1 mole of ethylene glycol with about 190 to about 250 mol % of 2-chloronitrobenzene at temperatures of about 40° to about 100° C. with the addition of an alkali metal hydroxide in dimethylacetamide.

16 Claims, No Drawings

PROCESS FOR THE PREPARATION OF 1,2-BIS-(2-NITROPHENOXY)-ETHANE

The invention relates to an improved process for the preparation of 1,2-bis-(2-nitrophenoxy)-ethane in high yield and very good technical purity by etherification of ethylene glycol with 2-chloronitrobenzene, the solvent for etherification being N,N-dimethylacetamide and the base required for etherification being introduced into the dimethylacetamide as a solid or as a suspension. The product obtained in this way may be reduced to 1,2-bis-(2-aminophenoxy)-ethane and further processed without purification.

1,2-bis-(2-nitrophenoxy)-ethane may be used as a fungicide (JP 48-010527). 1,2-bis-(2-nitrophenoxy)-ethane is also an important intermediate in the preparation of pigments. Thus, reduction to the corresponding diamine, tetraazotization and subsequent coupling thereof with 5-acetoacetylaminobenzimidazolones leads to valuable yellow pigments (EP-PS 0 024 702).

It is known that 1,2-bis-(2-nitrophenoxy)-ethane may be prepared by the reaction of potassium 2-nitrophenolate with 1,2-dichloroethane or 1,2-dibromoethane in alcohol (A. C. Cope, J. Am. Chem. Soc. 57 [1935] 572) or of sodium 2-nitrophenolate with 1,2-dichloroethane (A. Weddige, J. Prakt. Chem 21 [1880] 127) or with 1,2-dibromoethane in alcohol (R. Jaunin, R. Holl, Helv. Chim. Acta 41 [1958] 1783, 1789).

The application of these known processes on an industrial scale is impossible from the current standpoint. Thus, etherification with 1,2-dibromoethane is uneconomic due to the high cost of 1,2-dibromoethane. Furthermore, 1,2-dibromoethane, the 1,2-dichloroethane, is extremely harmful to health, so this compound must definitely be avoided in an industrial process, for occupational hygiene reasons. Furthermore, emissions of ethylene halides, which have a very high vapor pressure even at room temperature, cannot be avoided without the use of expensive apparatus. Also prohibitive for the reaction on an industrial scale is the formation of carcinogenic side products, such as vinyl chloride and vinyl bromide, which are produced under the previously mentioned reaction conditions of the disclosed processes. Finally, the above mentioned disclosed processes are also uneconomic from the point of view of yields (between 30 and 85%).

A well-known alternative to the previously mentioned disclosed processes for the preparation of 1,2-bis-(2-nitrophenoxy)-ethane is to react 63 parts of ethylene glycol with 315 parts of 2-chloronitrobenzene and 480 parts of a 50% strength aqueous sodium hydroxide solution at 90° C. in the presence of 80 parts of a 50% strength aqueous solution of benzyldimethyllaurylammonium chloride as phase transfer catalyst (DE 26 34, 419 Al). The dropwise addition of sodium hydroxide solution takes place over 3 hours and the final reaction requires 16 hours, which greatly reduces the economic viability of the process. The reaction mixture is added to 750 parts of water to precipitate the product, which is collected.

The purification of the crude product which is obtained by this process is unfavorable. The filter cake has to be slurried in 500 parts of water and adjusted to pH 3–4 with hydrochloric acid. The solid is then collected again and finally washed, first with 350 parts and then with 80 parts of acetone, and dried.

The disadvantages of the preparation variant mentioned are on the one hand the 400 mol % excess (relative to the ethylene glycol used) of sodium hydroxide, and on the other hand, and much more serious, the fact that an extremely alkaline effluent with a high concentration of salts, polluted with 2-nitrophenol (side product) and phase transfer catalyst which cannot be recycled, is produced.

There was therefore a need for an improved industrial process for the preparation of 1,2-bis-(2-nitrophenoxy)-ethane, which gives, in one process step, a product which can be separated as far as possible by simple filtration and avoids the disadvantages described above of known processes, in good yield and high purity.

Surprisingly, it has now been found that 1,2-bis-(2-nitrophenoxy)-ethane may be prepared in very good yield and high purity in a one-stage process by reacting 1 mole of ethylene glycol with about 190 to about 260 mol %, preferably with about 200 to about 250 mol %, in particular with about 210 to about 220 mol %, of 2-chloronitrobenzene at temperatures of about 40° to about 100° C., preferably of about 50° to about 80° C., in particular of about 55° to about 65° C., in the presence of an alkali metal hydroxide in dimethylacetamide (called "DMAc" in the following).

The alkali metal hydroxide is expediently used in an amount of about 200 to about 300 mol %, preferably of about 230 to about 260 mol %, in particular of about 240 to about 250 mol %, relative to the ethylene glycol. Although in principle all alkali metal hydroxides, such as lithium, sodium, potassium, rubidium or caesium hydroxide and mixtures thereof may be used, sodium hydroxide and/or potassium hydroxide are used for preference. The alkali metal hydroxides, such as preferably potassium hydroxide or sodium hydroxide, are introduced into the reaction mixture continuously or in portions, either as a solid or suspended in DMAc. The use of a suspension of sodium hydroxide in DMAc is particularly preferred.

Introduction of the alkali metal hydroxide generally takes between 2 and 4 hours. When the addition has finished, the mixture is stirred for about another 2 to 3 hours.

Finally, the reaction mixture, at the selected reaction temperature and with the aid of a pH electrode, is adjusted to a pH of 7.0 to about 5.5, preferably of about 6.5 to about 6.0, with a concentrated mineral acid. Suitable mineral acids are for example highly concentrated hydrochloric, hydrobromic, hydroiodic, sulfuric or phosphoric acid . The inorganic salts are filtered out of the hot reaction mixture and washed with DMAc. The product which has been produced is precipitated in the filtrate by adding water or lower aliphatic alcohols. It is collected and washed with water or alcohol. The water or alcohol and the DMAc are recovered from the filtrate by distillation and recycled to the production process.

The process according to the invention is expediently performed at atmospheric pressure. It may, however, also be carried out at elevated or reduced pressure (vacuum).

The process according to the invention is explained in more detail by the following example, but this does not represent a limitation.

EXAMPLE 700 parts of DMAc, 362 parts of 2-chloronitrobenzene and 68 parts of ethylene glycol are initially introduced into a 2 l Witt jar with stirrer, flow-breaker and internal thermometer and heated to 55° C. Then, at 55° C., a suspension of 108 parts of sodium hydroxide in 100 parts of DMAc is pumped in over the course of 4 hours at such a rate that the reaction temperature does not exceed 60° C. It is then stirred for a further 2.5 hours at 60° C. Then the reaction mixture is adjusted to pH 6.5 using 69 parts of 30% strength hydrochloric acid. After heating to 110° C., salt is filtered out of the reaction mixture under suction and this is then washed with 100 parts of DMAc. To crystallise the product, 300 parts of water are stirred into the filtrate at 90° C. The filtrate is cooled to 10° C. and the 1,2-bis-(nitrophenoxy)-ethane is filtered off under suction and washed with 100 parts of water. Water and DMAc are recovered from the filtrate by distillation and recycled to the production process. The moist, pale brown, crystalline product may be dried if necessary. The dried product, with a melting point of 167°–168° C., is obtained in a yield of 93% of theory and with a purity of 98.5%, according to HPLC.

If 151 parts of potassium hydroxide are used instead of 108 parts of sodium hydroxide, in 100 parts of DMAc, and if the reaction mixture is acidified to pH 6.5 with 58 parts of 96% strength sulfuric acid instead of 69 parts of 30% strength hydrochloric acid, the same result is obtained.

We claim:

1. A process for the preparation of 1,2-bis-(2-nitrophenoxy)-ethane, which comprises reacting 1 mole of ethylene glycol with about 190 to about 260 mol % of 2-chloronitrobenzene at temperatures of about 40° to about 100° C., with the addition of an alkali metal hydroxide, in dimethylformamide, the percentages being relative to ethylene glycol.

2. The process as claimed in claim 1, wherein the reaction is carried out at temperatures of about 50° to about 80° C.

3. The process as claimed in claim 1, wherein the reaction is carried out at temperatures of about 55° to about 65° C.

4. The process as claimed in claim 1, wherein the alkali metal hydroxide is added to the reaction mixture as a solid.

5. The process as claimed in claim 1, wherein the alkali metal hydroxide is added to the reaction mixture as a suspension in dimethylacetamide.

6. The process as claimed in claim 1, wherein the reaction is carried out with the addition of solid sodium hydroxide or potassium hydroxide or mixtures thereof.

7. The process as claimed in claim 1, wherein the reaction is carried out with the addition of sodium hydroxide or potassium hydroxide or mixtures thereof suspended in dimethylacetamide.

8. The process as claimed in claim 1, wherein the reaction is carried out with about 200 to 250 mol % of 2-chloronitrobenzene, relative to ethylene glycol.

9. The process as claimed in claim 1, wherein the reaction is carried out at with about 210 to about 220 mol % of 2-chloronitrobenzene, relative to ethylene glycol.

10. The process as claimed in claim 1, wherein the reaction is carried out with the addition of about 200 to about 300 mol % of alkali metal hydroxide, relative to ethylene glycol.

11. The process as claimed in claim 1, wherein the reaction is carried out with the addition of about 230 to about 260 mol % of alkali metal hydroxide, relative to ethylene glycol.

12. The process as claimed in claim 1, wherein the reaction is carried out with the addition of about 240 to about 250 mol % of alkali metal hydroxide, relative to ethylene glycol.

13. The process as claimed in claim 1, wherein the alkali metal hydroxide suspended in dimethylacetamide is added to the reaction mixture continuously or in portions.

14. The process as claimed in claim 1, further comprising adjusting the preparation to a pH of 6.5 to about 6.0 with concentrated hydrochloric acid or sulfuric acid.

15. The process as claimed in claim 1, wherein the reaction product is precipitated by the addition of water or a lower aliphatic alcohol.

16. The process as claimed in claim 1, wherein the reaction is carried out at atmospheric pressure or an elevated or reduced pressure.

* * * * *